(12) United States Patent
Radhakrishnan et al.

(10) Patent No.: US 9,119,956 B2
(45) Date of Patent: Sep. 1, 2015

(54) MEDICAL ELECTRODES WITH LAYERED COATINGS

(71) Applicant: Cardiac Pacemakers, Inc., St. Paul, MN (US)

(72) Inventors: Rajesh Radhakrishnan, Maple Grove, MN (US); Mary M. Byron, Roseville, MN (US); Angelo Fruci, Mahtomedi, MN (US); Brian Vance, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/085,735

(22) Filed: Nov. 20, 2013

(65) Prior Publication Data
US 2014/0142670 A1    May 22, 2014

Related U.S. Application Data

(60) Provisional application No. 61/729,320, filed on Nov. 21, 2012.

(51) Int. Cl.
*A61N 1/00* (2006.01)
*A61N 1/05* (2006.01)
*H01J 9/02* (2006.01)
*A61B 5/042* (2006.01)

(52) U.S. Cl.
CPC ... *A61N 1/05* (2013.01); *H01J 9/02* (2013.01); *A61B 5/042* (2013.01); *A61N 1/056* (2013.01)

(58) Field of Classification Search
CPC ...................................................... A61N 1/05
USPC ............................................................ 607/116
See application file for complete search history.

(56) References Cited

U.S. PATENT DOCUMENTS

| | | |
|---|---|---|
| 3,070,573 A | 12/1962 | Beck |
| 4,131,691 A | 12/1978 | Morley et al. |
| 4,212,719 A | 7/1980 | Osada et al. |

(Continued)

FOREIGN PATENT DOCUMENTS

| | | |
|---|---|---|
| EP | 0124200 B1 | 11/1984 |
| EP | 0585553 A1 | 6/1993 |

(Continued)

OTHER PUBLICATIONS

International Search Report and Written Opinion issued in PCT/US2013/071102, mailed Jun. 18, 2014, 16 pages.

(Continued)

*Primary Examiner* — Christopher D Koharski
*Assistant Examiner* — Nadia A Mahmood
(74) *Attorney, Agent, or Firm* — Faegre Baker Daniels LLP

(57) ABSTRACT

Various embodiments concern an electrode of an implantable medical device for delivering electrical stimulation to tissue. Such an electrode can include a main body formed from a substrate metal comprising one of titanium, stainless steel, a cobalt-chromium alloy, or palladium. The main body may not be radiopaque. The electrode may further include a first coating on at least one side of the main body, the first coating comprising a layer of one of tantalum or iridium metal that is at least about 2 micrometers thick. The first coating can be radiopaque and porous. The porosity of the first coating can increase the electrical performance of the electrode in delivering electrical stimulation to tissue.

20 Claims, 3 Drawing Sheets

(56) References Cited

U.S. PATENT DOCUMENTS

| | | | |
|---|---|---|---|
| 4,288,426 A | | 9/1981 | Stevens |
| 4,521,564 A | | 6/1985 | Solomon et al. |
| 4,536,179 A | | 8/1985 | Anderson et al. |
| 4,542,752 A | * | 9/1985 | DeHaan et al. ............... 607/119 |
| 4,603,704 A | * | 8/1986 | Mund et al. .................. 607/116 |
| 4,609,445 A | | 9/1986 | Collins |
| 4,632,842 A | | 12/1986 | Karwoski et al. |
| 4,656,083 A | | 4/1987 | Hoffman et al. |
| 4,687,482 A | | 8/1987 | Hanson |
| 4,720,512 A | | 1/1988 | Hu et al. |
| 4,946,903 A | | 8/1990 | Gardella et al. |
| 4,968,532 A | | 11/1990 | Janssen et al. |
| 5,026,607 A | | 6/1991 | Kiezulas |
| 5,041,100 A | | 8/1991 | Rowland et al. |
| 5,074,313 A | * | 12/1991 | Dahl et al. .................. 607/119 |
| 5,077,372 A | | 12/1991 | Hu et al. |
| 5,112,457 A | | 5/1992 | Marchant |
| 5,133,422 A | | 7/1992 | Coury et al. |
| 5,198,033 A | | 3/1993 | Kelley et al. |
| 5,277,753 A | | 1/1994 | Kelley et al. |
| 5,278,200 A | | 1/1994 | Coury et al. |
| 5,364,662 A | | 11/1994 | Domenico et al. |
| 5,376,400 A | | 12/1994 | Goldberg et al. |
| 5,494,712 A | | 2/1996 | Hu et al. |
| 5,593,550 A | | 1/1997 | Stewart et al. |
| 5,604,038 A | | 2/1997 | Denes et al. |
| 5,620,738 A | | 4/1997 | Fan et al. |
| 5,700,559 A | | 12/1997 | Sheu et al. |
| 5,702,754 A | | 12/1997 | Zhong |
| 5,782,908 A | | 7/1998 | Cahalan et al. |
| 5,789,018 A | | 8/1998 | Engelson et al. |
| 5,805,264 A | | 9/1998 | Janssen et al. |
| 5,811,151 A | | 9/1998 | Hendriks et al. |
| 5,849,368 A | | 12/1998 | Hostettler et al. |
| 5,866,113 A | | 2/1999 | Hendriks et al. |
| 5,914,115 A | | 6/1999 | Subramaniam |
| 5,919,570 A | | 7/1999 | Hostettler et al. |
| 6,015,597 A | | 1/2000 | David |
| 6,049,736 A | | 4/2000 | Stewart et al. |
| 6,053,171 A | | 4/2000 | Stewart et al. |
| 6,054,188 A | | 4/2000 | Tropsha et al. |
| 6,101,973 A | | 8/2000 | Stewart et al. |
| 6,129,956 A | | 10/2000 | Morra et al. |
| 6,169,127 B1 | | 1/2001 | Lohmann et al. |
| 6,180,191 B1 | | 1/2001 | Felts |
| 6,197,051 B1 | | 3/2001 | Zhong |
| 6,263,249 B1 | | 7/2001 | Stewart et al. |
| 6,306,165 B1 | | 10/2001 | Patnaik et al. |
| 6,549,811 B2 | | 4/2003 | Stewart et al. |
| 6,692,834 B1 | | 2/2004 | Martinez et al. |
| 6,713,568 B1 | | 3/2004 | Patnaik et al. |
| 7,123,969 B1 | * | 10/2006 | Chitre .......................... 607/121 |
| 7,217,286 B2 | | 5/2007 | Falotico et al. |
| 2007/0250142 A1 | | 10/2007 | Francis et al. |
| 2008/0280065 A1 | | 11/2008 | Fornsel et al. |
| 2011/0022160 A1 | | 1/2011 | Flanagan et al. |
| 2012/0123345 A1 | | 5/2012 | Felts et al. |
| 2012/0252709 A1 | | 10/2012 | Felts et al. |
| 2013/0296988 A1 | | 11/2013 | Weber et al. |
| 2014/0067028 A1 | | 3/2014 | Byron et al. |
| 2015/0039065 A1 | | 2/2015 | Weber et al. |

FOREIGN PATENT DOCUMENTS

| | | |
|---|---|---|
| EP | 1454651 B1 | 9/2004 |
| GB | 1326197 A | 8/1973 |
| WO | 8909246 A1 | 10/1989 |
| WO | WO03016589 A1 | 2/2003 |
| WO | WO2004103470 A1 | 12/2004 |
| WO | WO2009134901 A1 | 11/2009 |
| WO | WO2010104643 A2 | 9/2010 |
| WO | WO2011031316 A1 | 3/2011 |
| WO | WO2011143329 A2 | 11/2011 |
| WO | WO2011159975 A1 | 12/2011 |

OTHER PUBLICATIONS

Glocker, D.A., et al., "Tantalum radiopaque coatings for stents", 2008 Society of Vacuum Coaters, 51st Annual Technical Conference Proceedings, Chicago, IL, Apr. 19-24, 2008, pp. 199-204.

Partial International Search Report and Invitation to Pay Additional Fees issued in PCT/US2013/071102 mailed Feb. 17, 2014, 5 pgs.

International Search Report and Written Opinion issued in PCT/US2013/028692, mailed Sep. 18, 2013, 15 pages.

International Search Report and Written Opinion issued in PCT/US2013/054350, mailed Oct. 23, 2013, 11 pgs.

Karbushev, Valeriy V. et al., "Preparation of Polymer-Nanodiamond Composites with Improved Properties", Advanced Materials Research, vol. 59 (2009), pp. 275-278.

Liang, Xinhua et al., "Novel processing to produce polymer/Ceramic nanocomposites by Atomic Layer Deposition", J. Am Ceram. Soc., vol. 90, No. 1, pp. 57-63, 2007.

Maeng, W.J. et al., "Electrical property improvements of high-k gate oxide by in situ nitrogen incorporation during atomic layer deposition", Applied Physics Letters 90, 062909, 2007, 3 pages.

Partial International Search issued in International Application No. PCT/US2013/028692, mailed Jun. 6, 2013, 3 pages.

* cited by examiner

MEDICAL ELECTRODES WITH LAYERED COATINGS

CROSS-REFERENCE TO RELATED APPLICATION

This application claims priority to U.S. Provisional Application 61/729,320, filed Nov. 21, 2012, which is herein incorporated by reference in its entirety.

TECHNICAL FIELD

The present disclosure relates to medical devices having electrodes. More specifically, the present disclosure relates to coated electrodes.

BACKGROUND

An electrode can be provided on various implantable medical devices for sensing bioelectrical signals and/or delivering electrical stimulation. In some embodiments, one or more electrodes can be provided on an implantable lead. An implantable lead can be electrically connected to an implantable pulse generator (IPG). The IPG can include a power source and circuitry for sensing bioelectrical signals and/or delivering electrical energy to tissue. One or more electrodes can additionally or alternatively be provided on the housing of an IPG or other device, such as in a leadless implantable device.

Electrodes can be made of platinum-based materials, such as a platinum-iridium alloy. Platinum-based materials can have electrical performance characteristics suitable for biomedical applications. Also, an electrode formed from a platinum-iridium alloy can be radiopaque. However, platinum is a precious metal and the use of platinum as a base metal in an electrode can increase the cost of a medical device. There exists a need for alternatives to platinum-based electrodes that can match or exceed the electrical performance characteristics and/or radiopacity of platinum-based electrodes.

SUMMARY

Example 1 concerns a medical device for one or both of sensing signals from tissue and delivering stimulation to tissue. The medical device comprises an elongated body; a conductor extending within the elongated body; and an electrode exposed on an exterior of the elongated body. The electrode can comprise a main body, the main body formed from titanium and comprising a connector that is electrically and mechanically connected to the conductor; and a first coating on the main body, the first coating comprising a tantalum layer that is at least about 2 micrometers thick. The first coating allows the electrode to deliver the electrical stimulation to tissue such that the charge discharge capacitance (CDC) of the electrode is about 0.0004 farads per square centimeter or higher, the rate of voltage rise (dV/dt) of the electrode is about 0.05 volts per second or lower, and the impedance of the electrode is about 160 ohms or lower.

In example 2, the medical device of example 1, wherein the electrode further comprises a second coating on the first coating that further improves the performance of the electrode in delivering the electrical stimulation to tissue.

In example 3, the medical device of example 2, wherein the second coating is about 0.5-1.0 micrometers thick.

In example 4, the medical device of any of examples 2 or 3, wherein the second coating is formed from iridium-oxide.

In example 5, the medical device of any of examples 1-4, wherein the connector comprises a crimp coupling, the crimp coupling crimped over the conductor.

In example 6, the medical device of any of examples 1-5, wherein the main body is entirely within the elongated body such that only the first coating of the electrode is exposed on the exterior of the elongated body.

Example 7 concerns an electrode of a medical device. The electrode comprises a main body formed from a substrate metal comprising one of titanium, stainless steel, a cobalt-chromium alloy, or palladium; and a first coating at least on an outer surface of the main body, the first coating comprising a layer of one of tantalum, iridium, titanium, or platinum metal that is at least about 2 micrometers thick. The first coating is porous and the porosity of the first coating increases the electrical performance of the electrode in one or both of delivering electrical stimulation to tissue and sensing signals from tissue.

In example 8, the electrode of example 7, wherein the electrode further comprises a second coating provided over the first coating, the second coating increasing the electrical performance of the electrode in delivering electrical stimulation to tissue.

In example 9, the electrode of example 8, wherein the second coating is about 0.5-1.0 micrometers thick.

In example 10, the electrode of either of examples 8 or 9, wherein the second coating is formed from iridium-oxide.

In example 11, the electrode of any of examples 8-10, wherein the second coating is porous.

In example 12, the electrode of any of examples 7-11, wherein the main body is not radiopaque.

In example 13, the electrode of any of examples 7-12, wherein the porosity of the first coating substantially increases a charge discharge capacitance (CDC) performance characteristic of the electrode relative to the main body alone, and the porosity of the first coating substantially decreases an impedance value and a rate of voltage change (dV/dt) value of the electrode relative to the main body alone.

In example 14, the electrode of any of examples 7-13, wherein a charge discharge capacitance (CDC) of the electrical element is about 0.0004 farads per square centimeter or higher.

In example 15, the electrode of any of examples 7-14, wherein a rate of voltage change (dV/dt) value of the electrical element is about 0.05 volts per second or lower.

In example 16, the electrode of any of examples 7-15, wherein an impedance of the electrode is about 160 ohms or lower.

Example 17 concerns a method of fabricating an electrode of a medical lead having a conductor, the method comprising: forming a main body from a substrate metal comprising one of titanium, stainless steel, a cobalt-chromium alloy, or palladium, the main body having a first side and a second side, the second side configured to mechanically and electrically connect with the conductor; and depositing a first coating at least on the first side of the main body, the first coating comprising a layer of one of tantalum, iridium, titanium, or platinum metal. The first coating is at least about 2 micrometers thick, the first coating is porous, and the porosity of the first coating increases the electrical performance of the electrode in one or both of delivering electrical stimulation to tissue and sensing signals from tissue.

In example 18, the method of example 17, further comprising depositing a second coating on the first coating, the second coating comprising iridium-oxide, the second coating increasing the electrical performance of the electrode in discharging electrical energy to tissue.

In example 19, the method of example 18, wherein the second coating is about 0.5-1.0 micrometers thick.

In example 20, the electrode of either of examples 18 or 19, wherein depositing the first coating comprises depositing the radiopaque metal by glancing angle deposition.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
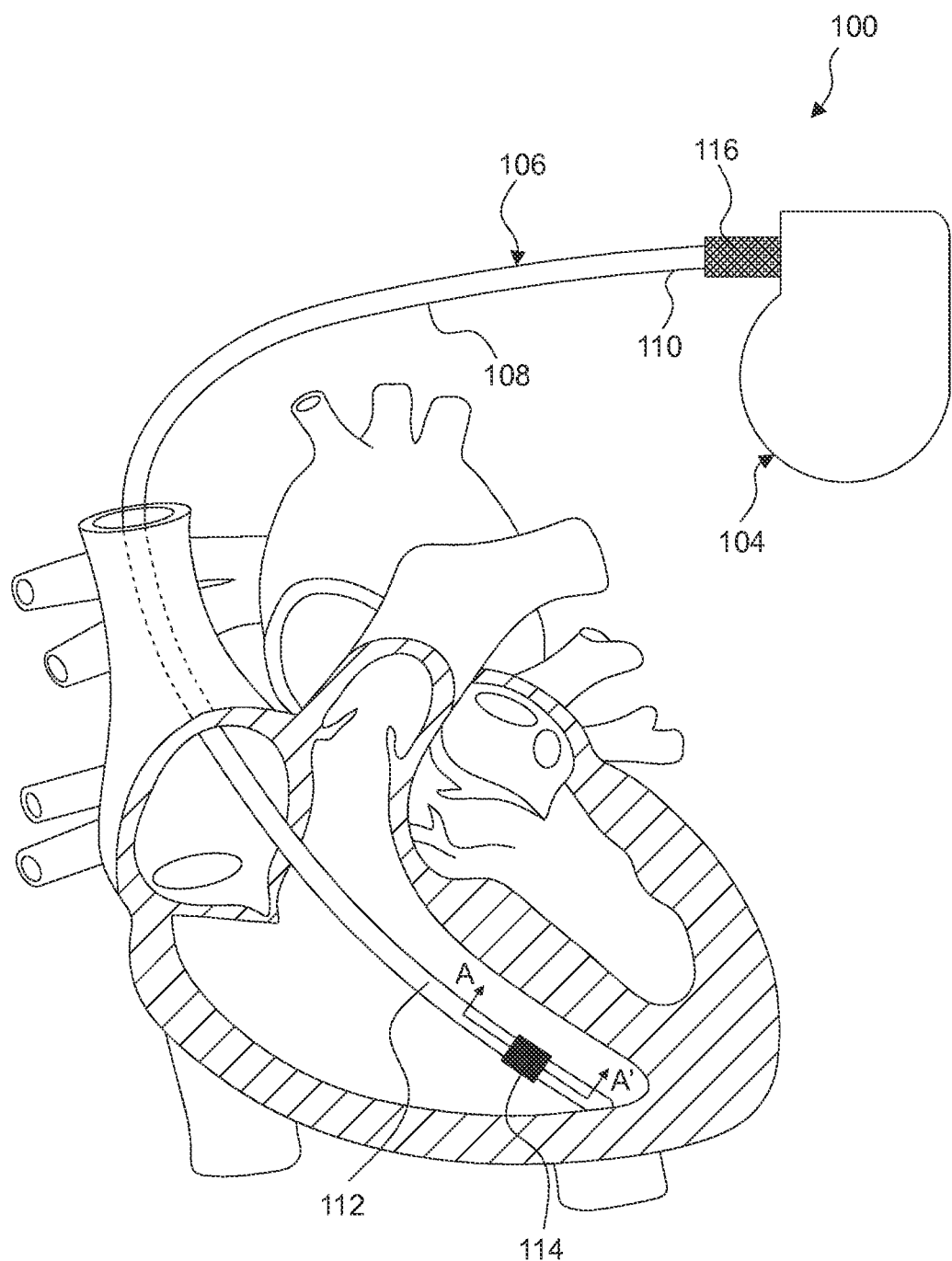
FIG. 1 is a schematic illustration of an implantable system having an implantable lead with an electrode.

While the subject matter of the present disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 for stimulating the heart. Embodiments of the system 100 can include an IPG 104 and an implantable lead 106 connected to the IPG 104. The IPG 104 can be configured to deliver electrical stimulation to the heart via the implantable lead 106. The electrical stimulation can include pacing, cardioversion, and/or defibrillation, among other therapies. The implantable lead 106 can include a proximal end portion 110 and a distal end portion 112. The implantable lead 106 can include a lead body 108. The lead body 108 can be a flexible tubular member formed from one or more polymer materials (e.g., polyurethane and/or silicone).

The IPG 104 can be implanted subcutaneously in the patient's chest, abdomen, or other location, depending on the application. Excess lead length, i.e., length beyond that needed to reach from a location of the IPG 104 to the desired implantation site, can be coiled up in a subcutaneous pocket (e.g., near the IPG 104). While the IPG 104 and the implantable lead 106 are illustrated for use in a cardiac therapy application, various embodiments of the present disclosure can be used for any other biomedical application involving sensing bioelectrical signals and/or delivering electrical energy (e.g., neurostimulation or ablation applications).

A plug-in 116 can be located on the proximal end portion 110 of the implantable lead 106. The plug-in 116 can be configured to provide an electrical and mechanical connection between the implantable lead 106 and the IPG 104. The IPG 104 can include a port (not shown) adapted to receive a portion of the plug-in 116 to establish the electrical and mechanical connection between the implantable lead 106 and the IPG 104. The implantable lead 106 can include an electrode 114 located on the distal end portion 112. The electrode 114 can be exposed on an exterior of the lead body 108 to deliver electrical stimulation to tissue.

Conventional electrodes can be made from a platinum-iridium alloy. The use of platinum as a base material can raise the cost of the electrodes due to the high value of platinum metal. Conventional platinum-iridium electrodes can be radiopaque due to the iridium component of the alloy. Furthermore, an iridium-oxide coating can be applied over the platinum-iridium alloy base to increase the electrical performance characteristics of the platinum-iridium electrode. The iridium-oxide coating forms a porous ceramic layer. The iridium-oxide coating is typically thin due to the ceramic nature of the coating. For example, the iridium-oxide coating may only be about 1-3 micrometers thick. It can be difficult to make the iridium-oxide coating thicker due to its ceramic form. In addition, a thicker iridium-oxide coating may become unstable and brittle. Even though the iridium-oxide coating contains iridium, the coating itself is not thick enough to be radiopaque under conventional imaging procedures. Rather, the much thicker platinum-iridium alloy base (e.g., several millimeters thick) makes such conventional electrodes radiopaque. Various embodiments of the present disclosure concern electrodes formed from a substrate metal other than platinum that is less expensive than platinum. As further discussed herein, one or more coatings can be provided on the substrate metal to match or exceed the electrical performance and radiopacity characteristics of platinum-based electrodes.

Figure 2:
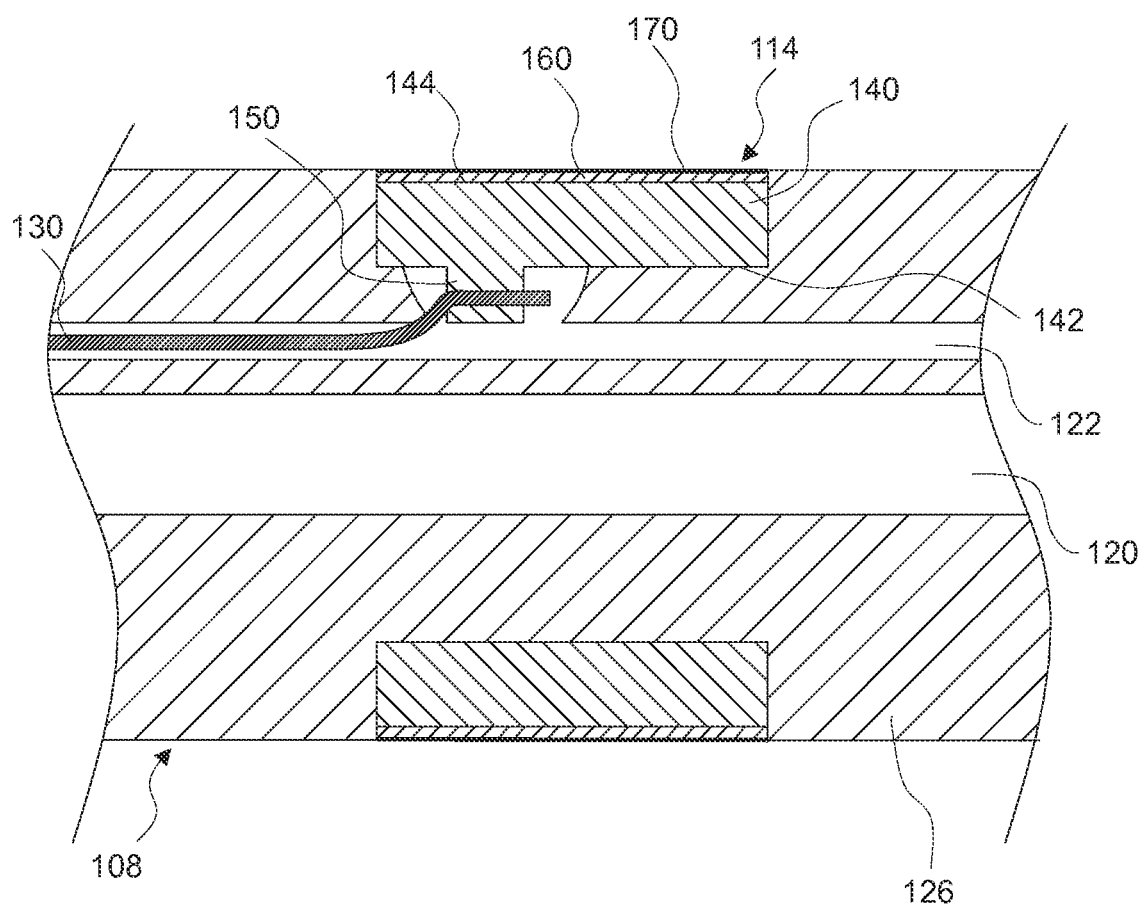
FIG. 2 is a cross-sectional view of an implantable lead and an electrode.

FIG. 2 shows a cross-sectional view of a portion of the implantable lead 106 along the line A-A' of FIG. 1. Specifically, FIG. 2 illustrates a cross-sectional view of the electrode 114 and the lead body 108 along the distal end portion 112 of the implantable lead 106. As shown, the lead body 108 can include a main lumen 120 and a conductor lumen 122 formed within the polymer material 126 of the lead body 108. The main lumen 120 can extend from the proximal end portion 110 to the distal end portion 112 within the lead 106. The conductor lumen 122 can extend from the proximal end portion 110 to at least the electrode 114, and may extend distally of the electrode 114. A conductor 130 can extend within the conductor lumen 122 from the proximal end portion 110 to at least the electrode 114. While the conductor 130 is shown as a cable in FIG. 2, any other type of conductor can be used. For example, a coil conductor could alternatively be used. The conductor 130 can extend to the plug-in 116 to electrically connect with a channel of the IPG 104.

The electrode 114 can include a main body 140. In various embodiments, the main body 140 is a ring structure having an inner surface 142 and an outer surface 144. As shown, the main body 140 is entirely within the lead body 108, i.e., the main body 140 is not exposed on the exterior of the lead 106. The main body 140 can be fully embedded within and/or beneath the polymer material 126 of the lead body 108. In various embodiments, the thickness of the main body 140 is about 0.25-1.00 millimeters. The main body 140 can comprise a vast majority of the electrode 114, such as 99 percent of the electrode 114 by weight or volume in some embodiments. The rest of the electrode 114 can comprise one or more coatings which are further discussed herein.

The main body 140 can be formed from a single substrate metal. In various embodiments, the substrate metal of the main body 140 is one of titanium, stainless steel, a cobalt-chromium alloy, or palladium. The main body 140, formed from these or other substrate metals, can be electrically conductive and non-radiopaque (e.g., the substrate metal of the main body 140 is not sufficiently radiopaque to clearly show up during a conventional imaging procedure).

The main body 140 of the electrode 114 can be electrically and mechanically coupled to the conductor 130. In various embodiments, the main body 140 includes a connector 150 that is integrated into or otherwise connected to the main body 140. For example, the connector 150 can be formed from the substrate metal. The connector 150 can be located on the inner surface 142 of the main body 140. The connector 150 can mechanically and electrically connect to the conductor 130. As shown in FIG. 2, the connector 150 can comprise a crimp coupling having a lumen in which the conductor 130 can be inserted. The connector 150 can then be crimped over the conductor 130. In this or in another way, the connector 150 can electrically and/or mechanically connect the conductor 130 to the main body 140 of the electrode. Various embodiments may not include the connector 150. In some embodiments, the conductor 130 can be welded to the main body 140 or other part of the electrode 114.

The main body 140 can reduce the cost of the electrode 114, relative to a platinum-iridium electrode, by being formed from one of the substrate metals discussed herein. However, the substrate metal of the main body 140 alone may have suboptimal electrical performance characteristics for some biomedical applications and may also not be radiopaque. One or more coatings can be applied over the substrate metal to improve electrical and radiopacity characteristics of the electrode 114. For example, a first coating 160 can be applied over the substrate metal of the main body 140.

The first coating 160 can be a metal coating. In some embodiments, the first coating 160 can be formed from a porous, radiopaque layer of metal. In various embodiments, the first coating 160 can be a layer of one of tantalum, iridium, or platinum. Other types of metal that can form a porous, radiopaque layer can also be used to form the first coating 160. The porosity of a first coating 160 can improve the electrical performance characteristics of the electrode 114 as compared to the electrode 114 being formed of the substrate metal alone. In addition, either of tantalum or iridium, for example, can be radiopaque in sufficient quantities, such as in the form of the first coating 160, to enable the electrode 114 to be seen in imaging modalities. Depending on the configuration, the first coating 160 can be disposed over the main body 140 by glancing angle deposition, physical vapor deposition (PVD), dip coating, electroplating, thermal decomposition, or other coating processes.

It is noted that the first coating 160, being a metal, can be malleable and robust. The malleability and robustness of the first coating 160 can allow the coating to be much thicker than a ceramic coating (e.g., iridium-oxide) which could otherwise become unstable and brittle. In some embodiments, the first coating 160 may be about 2 micrometers thick. In some embodiments, the first coating 160 may be about 2-5 micrometers thick. In some embodiments, the first coating 160 may be at least about 5 micrometers thick in some embodiments. In some embodiments, the first coating 160 may be about 5-15 micrometers thick. Such thicknesses are considerably larger than the 0.5 micrometer thickness of a ceramic iridium-oxide coating. The large thickness of the first coating 160 can allow the porosity of the first coating 160 to expose more surface area. For example, the voids of the porous metal can extend deeper because the coating itself is thicker. The greater amount of exposed surface area can increase the electrical performance characteristics of the electrode 114 (e.g., as compared to the main body 140 being uncoated). Moreover, the large thickness of the first coating 160 can allow the first coating 160 to be radiopaque.

The first coating 160 can be disposed on at least one side of the main body 140. As shown in FIG. 2, the first coating 160 can be disposed on the outer surface 144 (i.e. facing out from the interior of the lead 106) of the main body 140. In some embodiments, a second coating 170 can be provided over the first coating 160, as further discussed herein. In some other embodiments, the second coating 170 may not be included or may not extend over the entirety of the first coating 160, such that the first coating 160 is exposed on the exterior of the lead 106. The first coating 160 can be disposed along the entire outer surface 144 of the main body 140 (e.g., along the entire circumference of the main body 140 and from a proximal end to a distal end of the main body 140). In some embodiments, the first coating 160 can be disposed such that the substrate metal of the main body 140 is not exposed on the exterior of the lead 106. As such, in some embodiments, the first coating 160 may be the only exposed surface of the electrode 114. The other surfaces of the electrode 114 can be insulated within the lead body 108 by the polymer material 126. In some embodiments, only a portion of the outer surface 144 of the main body 140 may be covered by the first coating 160.

Although FIG. 2 illustrates the first coating 160 only being disposed along an outer surface 144 of the main body 140, the first coating 160 can be disposed along other surfaces of the main body 140. In some embodiments, the first coating 160 can be disposed along the inner surface 142. In some embodiments, the first coating 160 can be disposed along the connector 150. In some embodiments, the first coating 160 can be disposed along the proximal and/or distal facing surfaces of the main body 140. In some embodiments, all surfaces of the main body 140 can be entirely covered by the first coating 160. In some embodiments, every surface of the electrode 114 is defined by the first coating 160. In some cases, every surface of the electrode 114 exposed on the exterior of the lead 106 (or other device) is defined by the first coating 160. In some embodiments, the inner surface 142 of the electrode 114 is defined by the substrate material of the main body 140 (i.e. the inner surface is not coated with the first coating 160).

As shown in FIG. 2, a second coating 170 can be disposed over the first coating 160. For example, the second coating 170 can be disposed over the first coating 160 to define an exterior surface of the electrode 114. The second coating 170 can be an iridium-oxide coating. In some cases, the second coating 170 can be a platinum black coating. The second coating 170 can be ceramic. The second coating 170 can have a thickness of about 0.5-1.0 micrometers. The second coating 170 can be porous. The second coating 170 can increase the exposed surface area of the electrode 114 because the porous features of the second coating 170 can be finer than the porous features of the first coating 160. In some other embodiments, the second coating 170 is formed to be dense and non-porous (i.e. solid) by changing the process conditions (e.g., process power and process pressure) of applying the second coating 170. The second coating 170 can be applied by dip coating, PVD, sputtering, or other coating processes.

The second coating 170 can be disposed along the entirety of the first coating 160 (e.g., along every surface of the first coating 160). However, in some embodiments, only a portion of the first coating 160 may be covered by the second coating 170. In some embodiments, every surface of the electrode 114 is defined by the second coating 170. In some embodiments, every surface of the electrode 114 exposed on the exterior of the lead 106 (or other device) is defined by the second coating 170.

The thickness of a coating (e.g., the first coating 160 and/or the second coating 170) can be measured from one side of the coating (e.g., the side that is disposed directly over a substrate metal in the case of the first coating 160 or the side that is disposed directly over the first coating 160 in the case of the second coating 170) through the coating to the opposing side of the coating (e.g., the side exposed on an exterior of the lead or directly contacting the second coating 107). The thickness of a coating can refer to radial thickness. Such radial thickness can be measured along a dimension extending radially outward from the center axis of a lead toward the exterior, for example.

Although various exemplary electrode configuration options are presented herein, other electrode configuration options are contemplated. For example, the first coating 160 can be an iridium-oxide coating. In this case, the first coating 160 is a ceramic and may be thinner than some metal coatings. The iridium-oxide first coating 160 can be porous in some embodiments. In some other embodiments, the iridium-oxide first coating 160 can be formed to be dense and non-porous (i.e. solid). It is also noted that while a lead has been presented herein as an exemplar, an electrode in accordance with the present disclosure can be mounted on any medical device. For example, an electrode can be mounted on an elongated body, the elongate body comprising insulative material. The elongate body can be a lead, a catheter, or other medical device. The elongate body can comprise a polymer tube that defines a substantial majority of the exterior of the medical device, for example. The electrode can be used for delivering electrical stimulation to tissue and/or for sensing bioelectrical signals from tissue.

While a ring electrode has been used as an example herein to demonstrate the provision or one or more coatings on a main body formed from a substrate metal, the present disclosure is not so limited. The term electrode, as used herein, can refer to any of a segmented electrode, a housing electrode, a patch electrode, fixation helix or other electrically conductive fixation element, a coil (e.g., a defibrillation coil), or any other type of exposed electrical element configured for sensing bioelectrical signals and/or delivering electrical energy. In the case of a coil, the filars can be individually coated. Coated electrodes as referenced herein can be used in any biomedical application involving sensing bioelectrical signals and/or delivering electrical energy (e.g., cardiac, neurostimulation, or ablation applications, among others).

Various electrical performance characteristics can be used to evaluate electrode configurations. A first electrical performance characteristic is the charge discharge capacitance (CDC) of an electrode, which can be measured as farads per square area (i.e. $F/cm^2$). Generally, a higher CDC value indicates better electrical performance for biomedical applications. A second electrical performance characteristic of an electrode is the rate of voltage rise, which can be understood as change in voltage over unit time (i.e. dV/dt measured in volts/second). Generally, a lower dV/dt value is desired for biomedical applications. A third electrical performance characteristic of an electrode is impedance, measured in ohms. A small impedance value is generally desired for biomedical applications. The low impedance and high surface area (due to porosity) of electrodes of the present disclose can reduce low frequency noise and allow greater sensitivity of relevant signal data in sensing applications. Various electrode configurations are compared herein based on these electrical performance characteristics.

Figure 3:
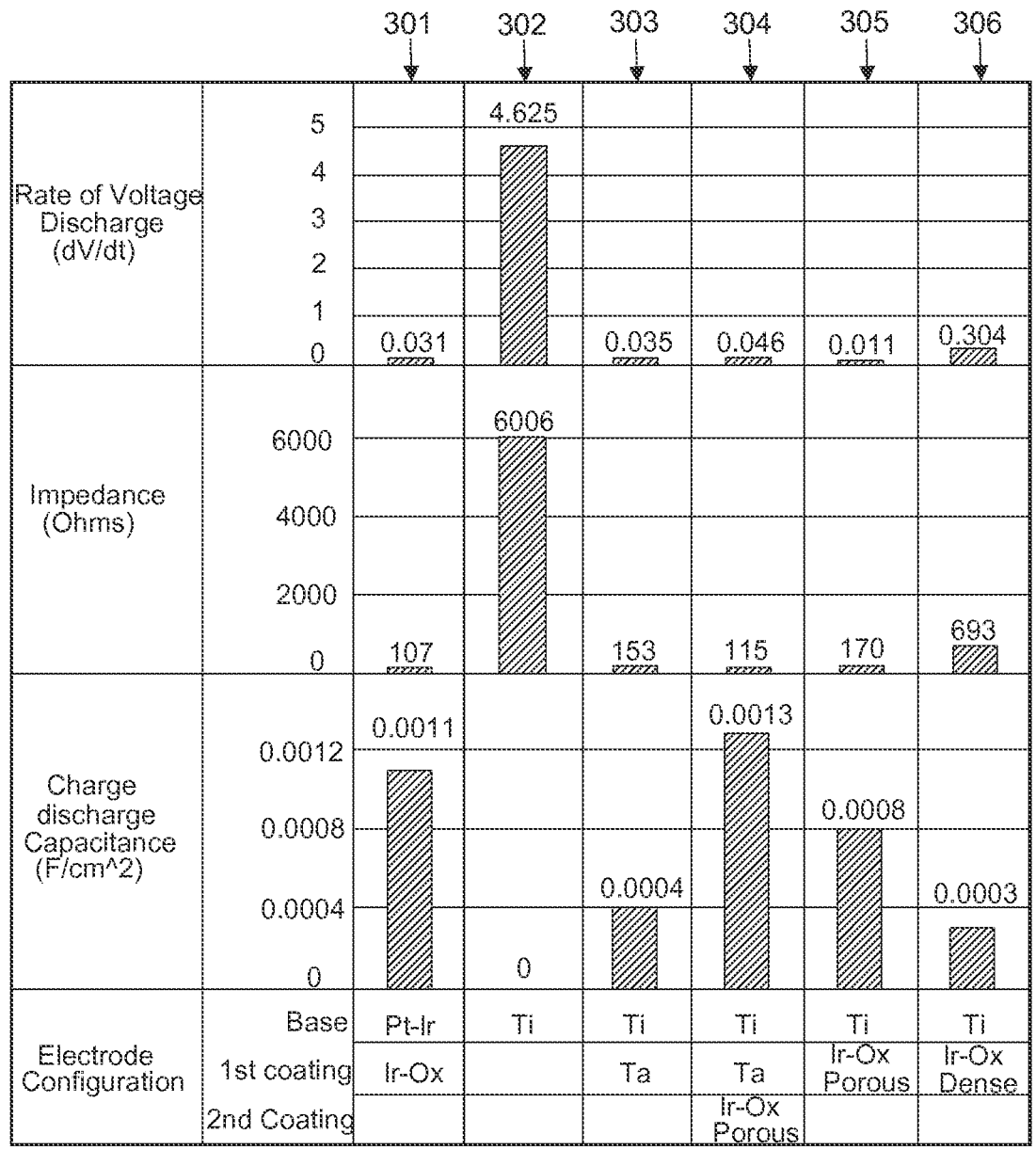
FIG. 3 is chart of test data characterizing electrical performance of various electrode configurations.

Tests show that a first coating over a substrate metal, and optionally a second coating over the first coating, as described herein, can substantially improve the electrical performance characteristics of an electrode compared to the substrate metal being uncoated. FIG. 3 illustrates a chart of data from a series of tests characterizing electrical performance characteristics of various electrode configurations as described herein. Specifically, the chart shows data for six different electrode configurations organized in six electrode configuration columns.

The first electrode configuration column 301 of FIG. 3 shows test data for a conventional platinum-iridium electrode with an iridium-oxide coating, which can represent a benchmark standard for other configurations as such electrodes are known to have good electrical performance characteristics. In the test, the conventional platinum-iridium electrode with an iridium-oxide coating was measured to have a CDC value of about $0.0011$ $F/cm^2$, a dV/dt value of about 0.031 V/s, and an impedance value of about 107 ohms.

The second electrode configuration column 302 shows test data for a titanium electrode with no coating modification (e.g., just the substrate metal of the main body). The test data of the second electrode configuration column 302 can represent baseline performance characteristic values for assessing performance improvements attributable to one or more coatings. In the test, the titanium electrode was measured to have a CDC value unperceivable to the testing equipment, a rate of voltage rise value of about 4.625 V/s, and an impedance value of about 6005 ohms.

The remaining electrode configuration columns of FIG. 3 show test data for electrodes having a titanium main body and one or more coatings on the titanium main body. Specifically, the third electrode configuration column 303 shows test data for a tantalum coating over a titanium main body. The test data shows that the tantalum coating improved the electrical performance characteristics of the electrode, as the electrode had a CDC value of about $0.0004$ $F/cm^2$, a rate of voltage rise value of about 0.035 V/s, and an impedance value of about 153 ohms.

In the case of a tantalum coating over a titanium main body, and an iridium-oxide coating over the tantalum coating, shown in the fourth electrode configuration column 304, a CDC value of about $0.0013$ $F/cm^2$, a rate of voltage rise value of about 0.046 V/s, and an impedance value of about 115 ohms were measured. As such, the iridium-oxide coating over the tantalum coating increased the electrical performance characteristics of the electrode to be similar to, or exceed, the electrical performance characteristics of the conventional iridium-oxide coated platinum-iridium electrode. Similar results may be achievable with various substrate metals for the main body 140, various metals for the first coating 160, and optionally various materials for the second coating 170, as described herein. The data results of the chart were particularly interesting because a titanium electrode body is not typically associated with high electrical performance characteristics. However, with one or more coatings as discussed herein, various substrate metals that are less expensive than platinum can form the major portion of electrodes suitable for biomedical applications without comprising electrical performance or radiopacity. Such use has the potential to reduce the cost and increase the availability of medical devices that rely on biocompatible and radiopaque electrodes with high electrical performance characteristics.

The fifth electrode configuration column 305 shows the electrical performance characteristics for a porous iridium-oxide coating as a first coating on a titanium main body. The first coating is not a metal coating in such a configuration. The sixth electrode configuration column 306 shows the electrical performance characteristics for a solid (i.e. non-porous) iridium-oxide coating as a first coating on a titanium main body. As such, an iridium-oxide coating over the substrate metal of a main body can improve the electrical performance characteristics of the electrode. Alternatively, either of the porous or dense iridium-oxide coatings can be disposed as a second coating over a tantalum, iridium, platinum, or other metal first coating.

Various modifications and additions can be made to the exemplary embodiments discussed herein without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device for one or both of sensing signals from tissue and delivering stimulation to tissue, the medical device comprising:
   an elongated body comprising insulative material;
   a conductor extending within the elongated body; and
   an electrode exposed on an exterior of the elongated body, the electrode comprising:
      a main body, the main body formed from titanium and comprising a connector that is electrically and mechanically connected to the conductor;
      a first coating disposed on the main body, the first coating comprising a tantalum layer that is at least about 2 micrometers thick, the tantalum layer porous; and
      a second coating disposed on the first coating, the second coating defining an exterior surface of the electrode, the second coating comprising iridium-oxide, the second coating porous,
      wherein the first and second coatings allow the electrode to deliver the electrical stimulation to tissue such that the charge discharge capacitance (CDC) of the electrode is about 0.0004 farads per square centimeter or higher, the rate of voltage rise (dV/dt) of the electrode is about 0.05 volts per second or lower, and the impedance of the electrode is about 160 ohms or lower.

2. The medical device of claim 1, wherein the second coating has finer porous features than the first coating.

3. The medical device of claim 1, wherein the second coating is about 0.5-1.0 micrometers thick.

4. The medical device of claim 2, wherein the second coating is disposed along the entirely of the first coating.

5. The medical device of claim 1, wherein the connector comprises a crimp coupling crimped over the conductor.

6. The medical device of claim 1, wherein the main body is entirely within the elongated body such that only the first and second coatings of the electrode are exposed on the exterior of the elongated body.

7. An electrode of a medical device, the electrode comprising:
   a main body formed from a substrate metal comprising one of titanium, stainless steel, a cobalt-chromium alloy, or palladium;
   a first coating at least on an outer surface of the main body, the first coating comprising a layer of one of tantalum, iridium, titanium, or platinum metal that is at least about 2 micrometers thick, the first coating porous; and
   a second coating provided over the first coating, the second coating comprising a porous ceramic layer having finer porous features than the first coating,
   wherein the first coating is porous, and the porosity of the first coating increases the electrical performance of the electrode in one or both of delivering electrical stimulation to tissue and sensing signals from tissue.

8. The electrode of claim 7, wherein the second coating increases the electrical performance of the electrode in delivering electrical stimulation to tissue.

9. The electrode of claim 7, wherein the second coating is about 0.5-1.0 micrometers thick.

10. The electrode of claim 7, wherein the second coating is formed from iridium-oxide.

11. The electrode of claim 7, wherein the second coating is disposed along the entirely of the first coating.

12. The electrode of claim 7, wherein the main body is not radiopaque.

13. The electrode of claim 7, wherein:
   the porosity of the first and second coatings substantially increase a charge discharge capacitance (CDC) performance characteristic of the electrode relative to the main body alone; and
   the porosity of the first and second coatings substantially decrease an impedance value and a rate of voltage change (dV/dt) value of the electrode relative to the main body alone.

14. The electrode of claim 7, wherein a charge discharge capacitance (CDC) of the electrical element is about 0.0004 farads per square centimeter or higher.

15. The electrode of claim 7, wherein a rate of voltage change (dV/dt) value of the electrical element is about 0.05 volts per second or lower.

16. The electrode of claim 7, wherein an impedance of the electrode is about 160 ohms or lower.

17. A method of fabricating an electrode of a medical device having a conductor, the method comprising:
   forming a main body from a substrate metal comprising one of titanium, stainless steel, a cobalt-chromium alloy, or palladium, the main body having a first side and a second side, the second side configured to mechanically and electrically connect with the conductor;
   depositing a first coating at least on the first side of the main body, the first coating comprising a layer of one of tantalum, iridium, titanium, or platinum metal, wherein the first coating is at least about 2 micrometers thick, the first coating is porous; and
   depositing a second coating on the first coating, the second coating porous and comprising iridium-oxide, the porosity of the first and second coatings increasing the electrical performance of the electrode in one or both of delivering electrical stimulation to tissue and sensing signals from tissue.

18. The method of claim 17, wherein the second coating has finer porous features than the first coating.

19. The method of claim 17, wherein the second coating is about 0.5-1.0 micrometers thick.

20. The method of claim 17, wherein depositing the first coating comprises depositing the second coating by glancing angle deposition.

* * * * *